US011752307B2

(12) United States Patent
Buller et al.

(10) Patent No.: US 11,752,307 B2
(45) Date of Patent: Sep. 12, 2023

(54) GUIDEWIRE AND CATHETER MANAGEMENT DEVICE AND RELATED METHODS

(71) Applicant: Teleflex Life Sciences Limited, Valletta (MT)

(72) Inventors: Christopher E. Buller, Toronto (CA); Joshua Brenizer, Oak Grove, MN (US)

(73) Assignee: Teleflex Life Sciences Limited, Valletta (MT)

( * ) Notice: Subject to any disclaimer, the term of this patent is extended or adjusted under 35 U.S.C. 154(b) by 288 days.

(21) Appl. No.: 17/154,535

(22) Filed: Jan. 21, 2021

(65) Prior Publication Data

US 2021/0308430 A1 Oct. 7, 2021

Related U.S. Application Data

(60) Provisional application No. 63/003,404, filed on Apr. 1, 2020.

(51) Int. Cl.
*A61M 25/09* (2006.01)
*A61M 39/06* (2006.01)
(Continued)

(52) U.S. Cl.
CPC ....... *A61M 25/09* (2013.01); *A61B 2046/234* (2016.02); *A61M 5/1418* (2013.01);
(Continued)

(58) Field of Classification Search
CPC .................. A61M 25/09; A61M 39/06; A61M 2025/09116; A61M 2209/084;
(Continued)

(56) References Cited

U.S. PATENT DOCUMENTS 3,805,770 A * 4/1974 Okada ...................... A61B 1/31
600/114
5,451,212 A 9/1995 Andersen
(Continued)

FOREIGN PATENT DOCUMENTS

WO 2008051898 B1 8/2008
WO 2009110803 A1 9/2009

OTHER PUBLICATIONS

Cable Comb Cable Organizing Tool, JONARD Tools, 2021 (Year: 2021).*
(Continued)

*Primary Examiner* — Brandy S Lee
*Assistant Examiner* — Kathleen Paige Farrell
(74) *Attorney, Agent, or Firm* — Robert B. Madden

(57) ABSTRACT

This patent document discloses accessory devices and associated methods for catheter and guidewire management in a surgical setting. Implementations can include an accessory device having a manually deformable body that includes proximal and distal surfaces. The body may further define at least first and second apertures, each aperture extending through the body. The first aperture can be engageable with a proximal end portion of a first elongate medical device, and the second aperture can be configured to receive a second elongate medical device. The body can be slidable along the proximal end portion of the first elongate medical device and/or the second elongate medical device, and the proximal surface of the body may include a funnel leading into the first aperture, the second aperture, or both. The body may be incorporated into, or attached to, a proximal side of a hemostasis valve utilized for a medical operation.

20 Claims, 6 Drawing Sheets

(51) Int. Cl.
*A61B 46/23* (2016.01)
*A61M 25/02* (2006.01)
*A61M 5/14* (2006.01)

(52) U.S. Cl.
CPC ............. *A61M 25/02* (2013.01); *A61M 39/06* (2013.01); *A61M 2025/024* (2013.01); *A61M 2025/09116* (2013.01); *A61M 2025/09125* (2013.01); *A61M 2209/084* (2013.01)

(58) Field of Classification Search
CPC .......... A61M 5/1418; A61M 2025/024; A61M 2025/09125; A61M 25/02; A61M 25/01; A61M 25/09041; A61M 25/0662; A61M 2039/062; A61M 25/0147; A61M 25/0113; A61M 25/0105; A61M 25/0043; A61M 2025/0293; A61B 2046/234; A61B 50/20; A61B 1/018; A61B 1/00087; A61B 46/23; A61B 90/57; A61B 1/01
See application file for complete search history.

(56) References Cited

U.S. PATENT DOCUMENTS

| | | | |
|---|---|---|---|
| 5,735,821 A | 4/1998 | Dobkin | |
| 5,795,335 A | 8/1998 | Zinreich | |
| 5,902,275 A | 5/1999 | Dobkin | |
| 7,637,863 B2* | 12/2009 | Deal et al. | A61B 1/012 |
| 8,523,824 B2 | 9/2013 | Teirstein et al. | |
| 10,321,933 B1 | 6/2019 | Ramee et al. | |
| 2006/0180714 A1 | 8/2006 | Mailhot | |
| 2008/0188890 A1* | 8/2008 | Weitzner et al. | A61M 25/09041 604/164.04 |
| 2010/0010475 A1 | 1/2010 | Teirstein et al. | |
| 2010/0274158 A1* | 10/2010 | Teirstein | A61M 25/09 |
| 2012/0271236 A1* | 10/2012 | Bruszewski | A61M 39/0613 604/167.03 |
| 2013/0041350 A1 | 2/2013 | Khoury | |
| 2015/0157829 A1* | 6/2015 | Bunch | A61M 25/02 604/174 |
| 2018/0369432 A1* | 12/2018 | Zaborsky | A61B 1/018 |
| 2021/0106790 A1* | 4/2021 | Chehab et al. | A61M 25/09 |
| 2021/0327612 A1* | 10/2021 | Park et al. | A61L 2/18 |

OTHER PUBLICATIONS

PCT International Search Report dated Jun. 17, 2021 in PCT application No. PCT/US2021/014392.
PCT Written Opinion dated Jun. 17, 2021 in PCT application No. PCT/US2021/014392.

* cited by examiner

GUIDEWIRE AND CATHETER MANAGEMENT DEVICE AND RELATED METHODS

CROSS-REFERENCE TO RELATED APPLICATION

This application is a non-provisional application that claims priority to U.S. Provisional Application Ser. No. 63/003,404, entitled "GUIDEWIRE AND CATHETER MANAGEMENT DEVICE AND RELATED METHODS" and filed Apr. 1, 2020, which is incorporated herein by reference in its entirety.

TECHNICAL FIELD

The subject matter of this patent document relates to the field of medical devices. More particularly, but not by way of limitation, the subject matter relates to accessory devices configured to receive and secure elongate medical devices, such as guidewires and catheters, during a medical operation.

BACKGROUND

Various medical procedures involve the insertion of one or more guidewires, catheters and/or other elongate devices into a patient. Invasive vascular procedures like balloon angioplasty and stent implantation, for example, require insertion of a guide catheter into the vasculature, usually in the femoral (leg) artery, and directing the catheter to the vasculature in need of treatment, such as vasculature of the heart. Through this catheter, a thin (for example 0.014 inch) wire called a guidewire, is introduced into and advanced through the artery to be treated. An additional catheter or other flexible elongate medical device can be introduced over, or alongside, the guidewire.

The catheter prior art is replete with variations, including "rapid exchange" catheters and "over-the-wire" catheters. In rapid exchange catheters, a guidewire enters a lumen in the distal tip of the catheter and then exits anywhere from about 1 cm to about 40 cm from the distal tip, running alongside the catheter but outside of the same. In over-the-wire catheters, the guidewire runs inside the catheter throughout its length.

At times, a clinician must treat or protect a vessels 3 using multiple fle elongate medical devices passed through the same guide catheter. In this circumstance, the operator passes two or more flexible elongate medical devices through the same Y adapter or hemostasis valve attached to the guide catheter's proximal end. The multiple flexible elongate medical devices travel down the same guide catheter and then enter the vessel requiring treatment, with each guidewire and its associated catheter, for example, entering a different vessel portion or branch vessel in need of treatment.

The multiple flexible elongate medical devices enter the guide catheter through the sealable entry site of the Y adapter or hemostasis valve. Since the multiple elongate medical devices have the same point of entry, the operator must take steps to keep them separate from each other, and to keep each properly identified. It is important to keep the flexible elongate medical devices separate for several reasons. If the elongate medical devices become twisted, they will interact with one another; for instance, when the clinician moves one guidewire or catheter, another guidewire or catheter may also move. Further, different, devices, such as stents, are typically passed over guidewires; therefore, if a guidewire becomes twisted with another elongate medical device, accurate advancement of the stent is inhibited. Also, because different devices are passed over different guidewires, the clinician must take steps to identify each wire so as not to confuse which wire is going down which vessel or branch vessel.

One approach to separating elongate medical devices is to place layers of sterile towels over the proximal end portions of the devices. However, towels are bulky and difficult to control. Towels securing guidewires also lie on the operative field and if the Y adaptor or hemostasis valve is moved, the towels tend to stay in place, so that the guidewires may be inadvertently pulled out of the vessel.

OVERVIEW

The present inventors recognize that preexisting methods of securing elongate medical devices during interventional operations are cumbersome and often ineffective. The present inventors further recognize that preventing the wrapping or twisting of guidewires and other elongate medical devices, especially when such devices are rotated during an operation, is difficult to achieve with currently available accessory devices.

The present accessory devices can retain guidewires, catheters, and other elongate medical devices in a manner that prevents such devices from wrapping or twisting during a medical procedure. The present accessory devices can be configured to manage elongate medical devices. An accessory device can include a body having proximal and distal surfaces and a thickness ranging from about 0.5 to about 3 centimeters, inclusive. The body can be manually deformable, and may have a Shore A durometer ranging between about 20 and about 60, inclusive. The device can also include at least first and second lumens or apertures extending through the body. The first aperture can be configured to be engageable with a proximal end portion of a first elongate medical device, and the second aperture can be configured to receive a second elongate medical device. The body of the accessory device can also be slidable along the proximal end portion of the first elongate medical device. The proximal surface of the body can include a funnel leading into the first aperture, the second aperture, or both. The body can be incorporated into, or attached to, a proximal side of a hemostasis valve. The body can also be clampable to the proximal end portion of the first elongate medical device. The second aperture can comprise a slit through the body, and the slit can be configured to secure a guidewire or other small diameter elongate medical device. One or both of the first and second apertures can include a clamping mechanism configured to attach and detach the device from the first or second elongate medical device. The clamping mechanism can comprise a slit extending from one or both of the first and second apertures to a perimeter of the body. The accessory device can include a deformable membrane positioned within the first or second aperture. A narrow slit may extend between the first and second apertures in some examples. A third aperture can also be included in an accessory device, positioned for example between the first and second apertures. The third aperture may have a larger diameter than the other two apertures. A first narrow slit can extend between the first aperture and the third aperture, and a second narrow slit can extend between the second aperture and the third aperture.

The present methods for securing elongate medical devices during a medical operation performed on a patient can involve advancing a first elongate medical device through a first aperture extending through a body of an accessory device positioned externally to the patient. The method may further involve securing a proximal portion of the first elongate medical device within the first aperture, and advancing a second elongate medical device through a second aperture that also extends through the body of the accessory device. The method can also involve securing a proximal portion of the second elongate medical device within the second aperture. Securing the proximal portion of the first elongate device within the first aperture can involve allowing the body of the accessory device to grip the proximal portion of the first elongate medical device. The proximal portion of the first elongate medical device can be removed from the first aperture by laterally sliding the proximal portion through a slit connecting the first aperture to a perimeter of the accessory device. The second aperture can comprise a narrow slit configured to frictionally secure the proximal portion of the second elongate medical device. The body of the accessory device can also include a funnel leading into the first aperture, the second aperture, or both.

Objects of the present accessory devices and related methods include, among others:
1. Securing one or more elongate medical devices during an operation;
2. Preventing the elongate medical devices from becoming wrapped, twisted or otherwise entangled with each other during the operation; and
3. Organizing the elongate medical devices in a manner that prevents the clinician from confusing one device for another during the operation.

These and other examples and objects of the present accessory devices and related methods will be set forth in the following Detailed Description. This Overview is intended to provide non-limiting examples of the present subject matter—it is not intended to provide an exclusive or exhaustive explanation. The Detailed Description below is included to provide further information about the present accessory devices and related methods.

BRIEF DESCRIPTION OF THE DRAWINGS

In the drawings, like numerals can be used to describe similar features and components throughout the several views. The drawings illustrate generally, by way of example but not by way of limitation, various embodiments discussed in the present patent document.

Figure 1A:
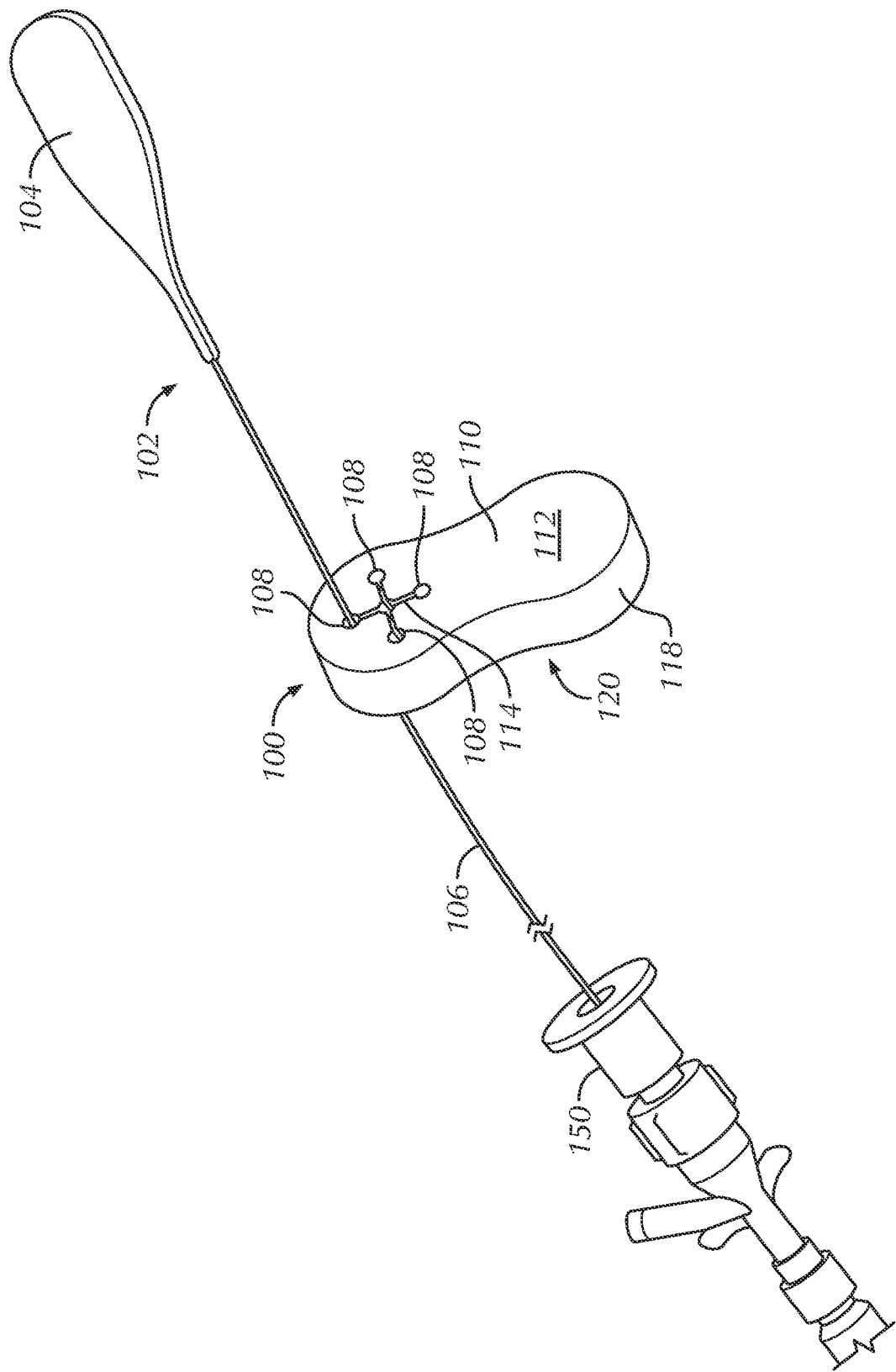
FIG. 1A illustrates a perspective view of a guide extension catheter engaged with an accessory device, as constructed in accordance with at least one embodiment.

The drawing figures are not necessarily to scale. Certain features and components may be shown exaggerated in scale or in schematic form and some details may not be shown in the interest of clarity and conciseness.

DETAILED DESCRIPTION

The present accessory devices and associated methods provide clinicians with a means to treat a range of vascular abnormalities, including vessel damage and/or complications related to CTO angioplasty interventions, without accidentally wrapping, twisting or otherwise entangling the elongate medical devices necessary to treat such abnormalities. The present accessory devices and associated methods provide means to retain, secure and organize various elongate medical devices during an operation. Such elongate medical devices may include, but are not limited to, catheters and/or guidewires. The present accessory devices and associated methods are not limited to any particular operation. Accordingly, the present accessory devices and associated methods may be implemented pursuant to treating an assortment of vascular abnormalities, including but not limited to vascular lesions, including partial or total blockages and any associated damage, vascular perforations, among other conditions. Unlike preexisting devices, the disclosed accessory devices can be secured to an in-place elongate medical device, instead of the operating field, e.g., the patient's surgical drape.

As used herein, "accessory device" means a device that does not directly effect a medical treatment and is separate from the interventional devices, e.g., guidewires and catheters, that do effect a medical treatment. The accessory devices disclosed herein are uniquely configured to support various elongate medical devices during their employment in a medical operation. In this capacity, the present accessory devices may prevent elongate medical devices from becoming wrapped or twisted, thereby improving the safety, effectiveness, and/or efficiency of a medical operation.

For ease of illustration, the terms "interventional device" and "medical device" are used interchangeably herein. Non-limiting examples of medical/interventional devices accommodated by the accessory devices described herein include guidewires, single-, double- and/or multi-lumen catheters, guide extension catheters, balloon catheters, stent catheters, ablation devices, elongate sheaths, and combinations thereof.

FIG. 1A illustrates a first embodiment of the accessory device 100, shown engaged with a guide extension catheter device 102. As shown, the guide extension catheter device 102 can include a proximal tab 104 attached to an elongate push member (e.g., push wire) 106. The elongate push member 106 is inserted through one of a plurality of peripheral lumens or apertures 108 defined by a body 110 of the accessory device 100, each of the peripheral apertures 108 being visible at a proximal surface 112 of the accessory device 100. A narrow slit 114 can connect each peripheral aperture 108 to a central lumen or aperture 116, and a lateral surface 118 of the device extends between the proximal surface 112 and the distal surface 120. In various embodiments, lateral surface 118 extends as a continuous perimeter of the body, and is unbroken around the perimeter of the accessory device 100. In use, the accessory device WO is positioned outside the patient. The accessory device 100 may be positioned proximal to a hemostasis valve 150, e.g., about 0.0 to about 5.0 inches from the hemostasis valve 150, and in some examples, the body 110 of the accessory device 100 may be incorporated into, or attached to, a proximal side of a hemostasis valve 150.

The peripheral apertures 108, the central aperture 116, and the slits 114 define through-lumens that extend through the entire body 110 of the accessory device 100, such that elongate medical devices, e.g., the guide extension catheter device 102, can be inserted at the proximal surface 112, pushed through the body 110, and extended beyond the distal surface 120 into a patient. The body 110 can thus be slidable along at least a portion of the guide extension catheter device 102 to allow its insertion and removal.

Each of the peripheral apertures 108, via flexing of the slit 114 connected thereto, may be expanded or urged open to accommodate insertion of the elongate push member 106 and in some examples, a portion of the proximal tab 104, into the peripheral aperture 108, which will then close back around the push member 106 and/or proximal tab 104 to hold it in place. In this manner, the size and shape of each peripheral aperture 108, in combination with the manually deformable material constituting the body 110 of the accessory device 100, can be configured to grip at least a proximal portion of the guide extension catheter device 102, e.g., the proximal tab 104, and prevent it from moving proximally or distally unless a sufficient pulling or pushing force is deliberately applied from a proximal end of guide extension catheter device 102 by a clinician. The accessory device 100 is thus configured to receive and secure the guide extension catheter device 102 by frictionally holding the push member 106 and/or the proximal tab 104 within a slit 114 and/or an aperture 108 defined by the accessory device 100.

In some examples, the central lumen or aperture 116 may be configured to receive an elongate medical device, which is then moved laterally through one of the slits 114 to a peripheral aperture 108. In additional examples, the central aperture 116 can also be configured to retain at least a portion of an elongate medical device during an operation. The size and/or shape of the central aperture 116 may thus be substantially the same or different than one or more peripheral apertures 108. For example, the central aperture 116 may define a larger diameter than the peripheral apertures 108 to facilitate the initial insertion of an interventional device therein.

In some embodiments, the slits 114 may be utilized for securing an interventional device, while the peripheral apertures 108 and/or central aperture 116 may be used for maintaining separation between the interventional devices while one or more of such interventional devices are moved distally or proximally. For example, a clinician may advance a guidewire distally through a first peripheral aperture 108. When a distal end of the guidewire reaches its anatomical target site, the clinician may move a proximal portion of the guidewire laterally into the slit 114 adjacent to the first peripheral aperture 108. The more narrow diameter of the slit 114 may effectively retain and secure the guidewire within the slit 114, such that it remains stationary while the clinician proceeds to move another interventional device proximally or distally through a second peripheral aperture 108.

Each of the peripheral apertures 108 and/or the central aperture 116 can accommodate an interventional device, such that the accessory device 100 can retain at least five interventional devices at one time in the embodiment shown. By maintaining a lateral separation between each of the simultaneously retained interventional devices, the accessory device 100 can prevent twisting or wrapping of the interventional devices. The portion of each interventional device retained by the accessory device 100 may have a unique cross-sectional shape and/or diameter, such that each peripheral aperture 108 and the slit 114 connected thereto may flex to a different degree. The diameter of the cross-section of each peripheral aperture 108 and the central aperture 116 can be selected to closely grip the diameter of each interventional device, or it can be larger. If the diameter of an aperture is larger than the diameter of the interventional device, it can allow the interventional device to move proximally and distally with respect to the accessory device 100. This may be desirable for some devices, such as balloon catheters. One or more of the peripheral apertures 108 and/or the central aperture 116 can also include a deformable membrane to improve the fit between the apertures and any interventional devices advanced therethrough. The peripheral apertures 108 and the central aperture 116 are shown having circular cross-sections. In embodiments, the cross-sectional shape of the apertures may vary, for example to accommodate interventional devices having different cross-sectional shapes. Accordingly, the cross-sectional shape of one or more apertures may be irregular in shape, or approximately rectangular, triangular, oval, square, or fan shaped.

The body 110 of the accessory device 100 may be constructed of a firm but flexible material, such as a deformable and/or elastomeric material. For elastomeric materials, the material properties of an elastomer may be such that the material may "cold-flow," or form itself around the surface of an interventional device, such as the proximal tab 104 or push member 106. In some examples, the accessory device 100 may be formed at least in part of a rubber-like material, which may comprise a polymer composition. The material may be tear-resistant, slip-resistant and resilient, such that the accessory device 100 does not readily slide on a flat surface and retains its original shape after repeated bending and flexing. The durometer of the material may be measured as a Shore A value of about 40, or a value ranging from less than 20 to about 20, about 25, about 30, about 35, about 40, about 45, about 50, about 55, about 60, greater than 60, or any value therebetween. In specific examples, one or more materials used to construct the accessory device 100 can include AGILUS30, which is sold by Stratasys, Ltd. The accessory device 100 may be reusable or single-use disposable.

Figure 1B:
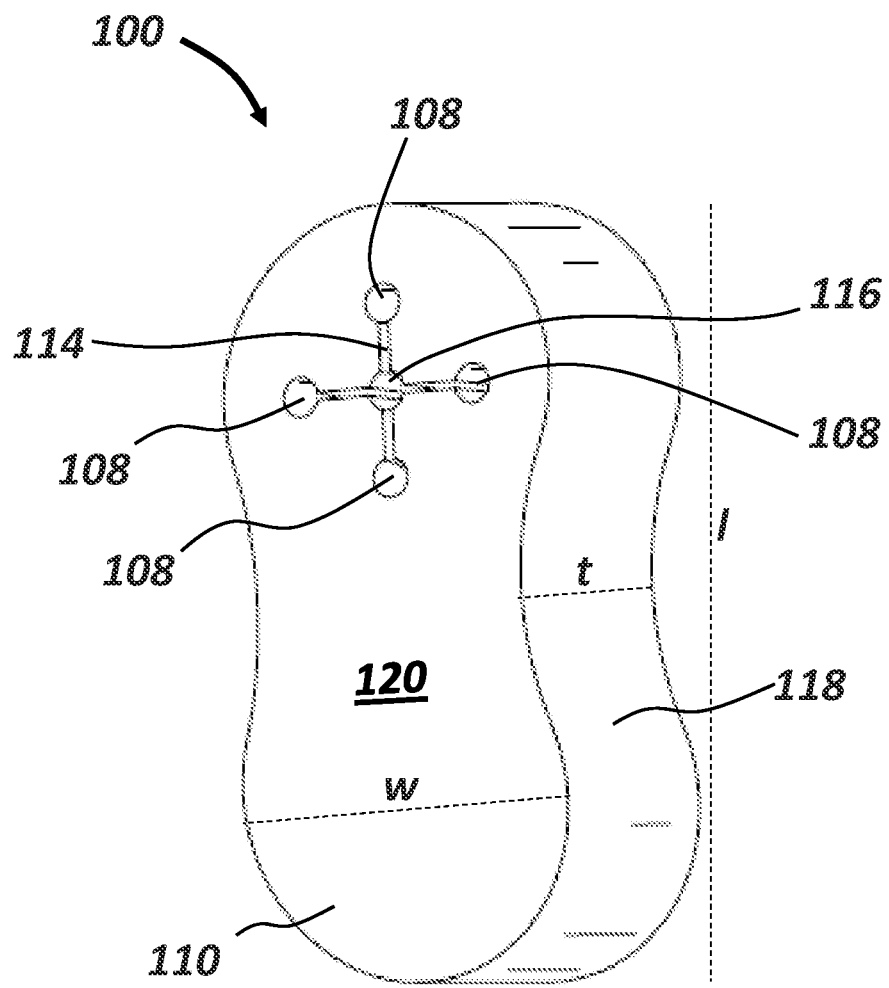
FIG. 1B illustrates an enlarged perspective view of a distal surface of the accessory device shown in FIG. 1A.

FIG. 1B illustrates an enlarged view of the accessory device 100, showing its distal surface 120 and the thickness t of the body 112. The shape, dimensions, and arrangement of features shown in FIG. 1B may vary. In the embodiment shown, for example, the peripheral apertures 108 are equidistant from each other and the central aperture 116 in an arrangement resembling a pinwheel. The distance between each aperture, whether or not they are arranged peripherally or centrally with respect to each other, may be sufficient to prevent or at least reduce undesirable instances of wrapping or twisting between the interventional devices concurrently positioned or advanced through the accessory device 100. The distance between each peripheral aperture 108 and/or the central aperture 116 may vary in different embodiments, for example ranging from about 0.10 centimeters to about 0.15 centimeters, about 0.20 centimeters, about 0.25 centimeters, about 0.30 centimeters, about 0.35 centimeters, about 0.40 centimeters, about 0.45 centimeters, about 0.5 centimeters, about 0.6 centimeters, about 0.7 centimeters, about 0.8 centimeters, about 0.9 centimeters, about 1.0 centimeter, about 1.5 centimeters, about 2.0 centimeters, about 2.5 centimeters, about 3.0 centimeters, about 3.5 centimeters, about 4.0 centimeters, about 4.5 centimeters, about 5.0 centimeters, greater than 5.0 centimeters, or any distance therebetween. Additional examples may include an arrangement of apertures designed specifically for a particular collection of interventional devices. Such embodiments may feature variously sized apertures, with some apertures arranged closer together than others. For instance, apertures may be clustered in pairs or groups to enable certain interventional devices to be maintained in closer proximity than others. Paired interventional devices may include one or more catheters paired with one or more guidewires, for example.

The peripheral apertures 108 and/or the central aperture 116 may have a constant diameter, or a diameter that changes along a length of each aperture, such that a particular aperture may define a uniform tube or a tapered funnel. Funneled apertures may differ in their angular taper, such that the apertures have only a slight taper or a larger taper. Larger tapers may be appropriate for many catheters (with a typical size being on the order of 0.020 to 0.040 inches), while smaller tapers may be appropriate for many guidewires (with a typical size being on the order of 0.014 inches). Tapered apertures may have a larger diameter at the proximal surface 112 than the distal surface 120. The larger proximal diameter may facilitate insertion of the distal end of an elongate interventional device, especially an elongate interventional device having a wider diameter relative to a guidewire, for example.

The overall size and/or shape of the accessory device 100 may also vary. The accessory device 100 may be advantageously smaller than preexisting devices utilized to retain interventional devices, making the accessory device 100 easier to handle and less intrusive than other devices and reducing the likelihood that the accessory device 100 will interfere with other devices during an operation. The accessory device 100 shown in FIG. 2B has a length l of about 2.0 inches and a thickness of about 0.375 inches (~0.95 cm). In embodiments, the length l may range from less than 1.0 inch to about 1.0 inch, about 1.25 inches, about 1.50 inches, about 1.75 inches, about 2.0 inches, about 2.25 inches, about 2.50 inches, about 2.75 inches, about 3.0 inches, about 3.25 inches, about 3.50 inches, about 3.75 inches, about 4.0 inches, about 4.25 inches, about 4.5 inches, about 4.75 inches, about 5.0 inches, greater than 5.0 inches, or any length therebetween. The thickness t, as measured from the proximal surface 112 to the distal surface 120, may range from less than about 0.50 centimeters to about 0.5 centimeters, about 0.75 centimeters, about 1.0 centimeter, about 1.25 centimeters, about 1.50 centimeters, about 1.75 centimeters, about 2.0 centimeters, about 2.25 centimeters, about 2.50 centimeters, about 2.75 centimeters, about 3.0 centimeters, about 3.25 centimeters, about 3.50 centimeters, about 3.75 centimeters, about 4.0 centimeters, about 4.25 centimeters, about 4.50 centimeters, about 4.75 centimeters, about 5.0 centimeters, about 6.0 centimeters, about 7.0 centimeters, about 8.0 centimeters, about 9.0 centimeters, about 10.0 centimeters, more than 10.0 centimeters, or any thickness therebetween.

The width w may vary along the length l of the accessory device 100. In the embodiment shown, the width w is most narrow near the middle of the accessory device 100. Additional examples may have a constant or substantially constant width w along the length l of the device, or one maximum width w near the middle of the device, or one maximum width w near one end of the device. The shape of the accessory device 100 defined by the width w may be advantageously ergonomic, such that a clinician can hold and maneuver the accessory device 100 using one hand with ease. In various examples, the accessory device 100 can be symmetrical or asymmetrical, oblong or irregular in shape, or approximately rectangular, triangular, oval, circular, square, or fan shaped. The accessory device 100 may also be complementary in size and shape to a portion of another object, such as a piece of operating room equipment, e.g., an operating table or rail, or an anatomical feature of the patient, e.g., a patient's extremity. According to such embodiments, the accessory device 100 can remain stationary when placed on an object by the clinician.

Figure 2A:
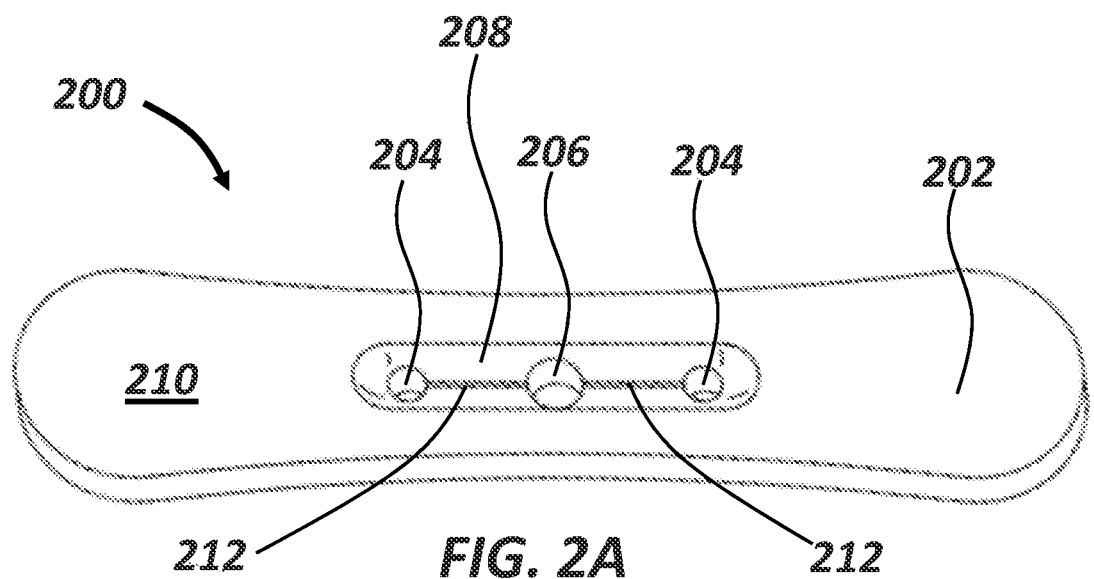
FIG. 2A illustrates an enlarged perspective view of a proximal surface of another accessory device, as constructed in accordance with at least one embodiment.

An example of an accessory device defining a taper or funnel is shown in FIG. 2A. As shown, the accessory device 200 includes a body 202 defining only two peripheral apertures 204 and one central aperture 206 positioned at the bottom of a recessed portion or funnel 208, which is visible at the proximal surface 210 of the device 200. A narrow slit 212 connects each peripheral aperture 204 to the central aperture 206.

The funnel 208 can facilitate insertion of an elongate interventional device through the accessory device 200 by receiving and guiding the elongate interventional device into one of the peripheral apertures 204 and/or the central aperture 206. In some embodiments, an interventional device may be inserted initially through the central aperture 206 and then moved laterally through one of the slits 212 to a peripheral aperture 204. As shown in this particular example, the central aperture 206 may have a larger diameter than either of the peripheral apertures 204, making the central aperture 206 easier to target with the distal end of an elongate interventional device. As the elongate interventional device is moved laterally through a slit 212 to one of the peripheral apertures 204, the slit 212 may expand around the larger cross-sectional diameter of the elongate interventional device. After reaching a peripheral aperture 204, the slit 212 through which the device passed may return to its resting width, such that the elongate interventional device cannot pass back through the slit 212 toward the central aperture 206 unless it is urged to do so by the clinician, which may occur during removal of the elongate interventional device from the patient and/or upon a distal end of the interventional device reaching its target anatomical site.

Figure 2B:
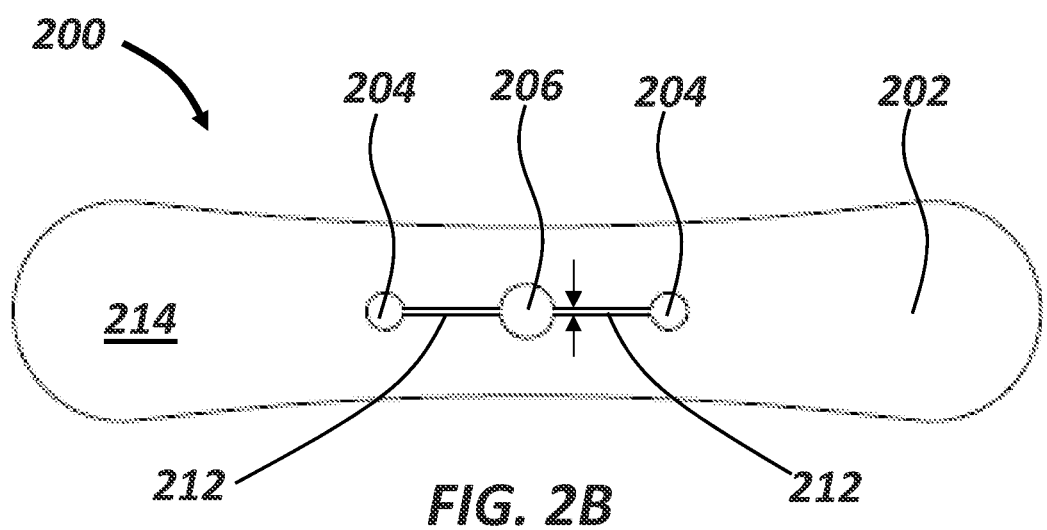
FIG. 2B illustrates an enlarged view of a distal surface of the accessory device shown in FIG. 2A.

FIG. 2B shows the distal surface 214 of the accessory device 200. The central aperture 206 is visible, flanked by the two peripheral apertures 204 via slits 212. The funnel 208 is not visible at the distal side 214 in this particular example, although in additional embodiments the body 202 of the accessory device 200 may be recessed on both sides around the apertures 204, 206. According to some of such embodiments, the proximal and distal surfaces may be identical or substantially identical.

The width of each slit 212, labeled by the opposing arrows in FIG. 2B, may be narrow to prevent unintentional lateral sliding of an interventional device from one aperture to the next and/or to tightly secure a proximal end portion of an interventional device during an operation, thereby preventing the interventional device from moving distally or proximally in the absence of clinician-applied force. In embodiments, the width of the slit 212 may range from less than about 1 millimeter to about 1 millimeter, about 2 millimeters, about 3 millimeters, about 4 millimeters, about 5 millimeters, about 6 millimeters, about 7 millimeters, about 8 millimeters, about 9 millimeters, about 10 millimeters, more than 10 millimeters, or any width therebetween. The narrow width of each slit 212, in combination with the material(s) used to form the accessory device 200, may configure the slit 212 to retain and secure at least a portion of a guidewire or other small-diameter interventional device. The width of each slit 212 shown in FIGS. 2A and 2B may be the same or similar to the width of each slit 114 shown in FIGS. 1A and 1B, along with the width of the slit discussed below in connection with FIG. 3.

The accessory device 200 shown in FIGS. 2A and 2B provides one example of the many variations in size and/or shape that may be implemented in accordance with the present disclosure. Compared to the accessory device shown in FIGS. 1A and 1B, the accessory device 200 is more elongate and defines a more narrow width. The apertures 204, 206 are also included near the central portion of the accessory device 200, unlike the peripheral apertures 108 and central aperture 116 of the accessory device 100, demonstrating that the apertures can vary in position, number and/or size in different embodiments to accommodate different numbers and types of elongate interventional devices.

Figure 2C:
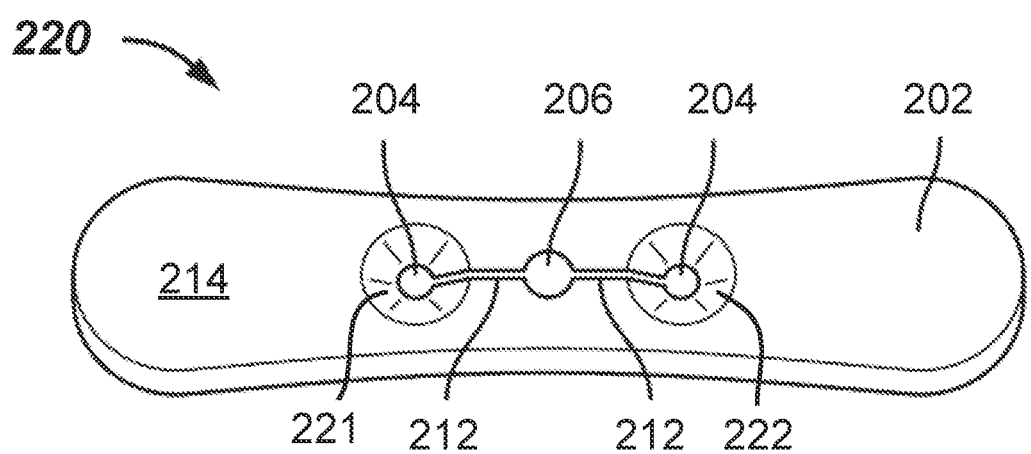
FIG. 2C illustrates an enlarged perspective view of a proximal surface of another accessory device, as constructed in accordance with at least one embodiment.

FIG. 2C illustrates an enlarged perspective view of a proximal surface of another accessory device 220, as constructed in accordance with at least one embodiment. Accessory device 220 include features corresponding to the features of accessory 200 as illustrated and described with respect to FIGS. 2A and 2B, but with the difference in having a first funnel 221 surrounding only a first one of the apertures 204 and a second funnel 222 surrounding only a second and different one of the apertures 204.

Figure 3:
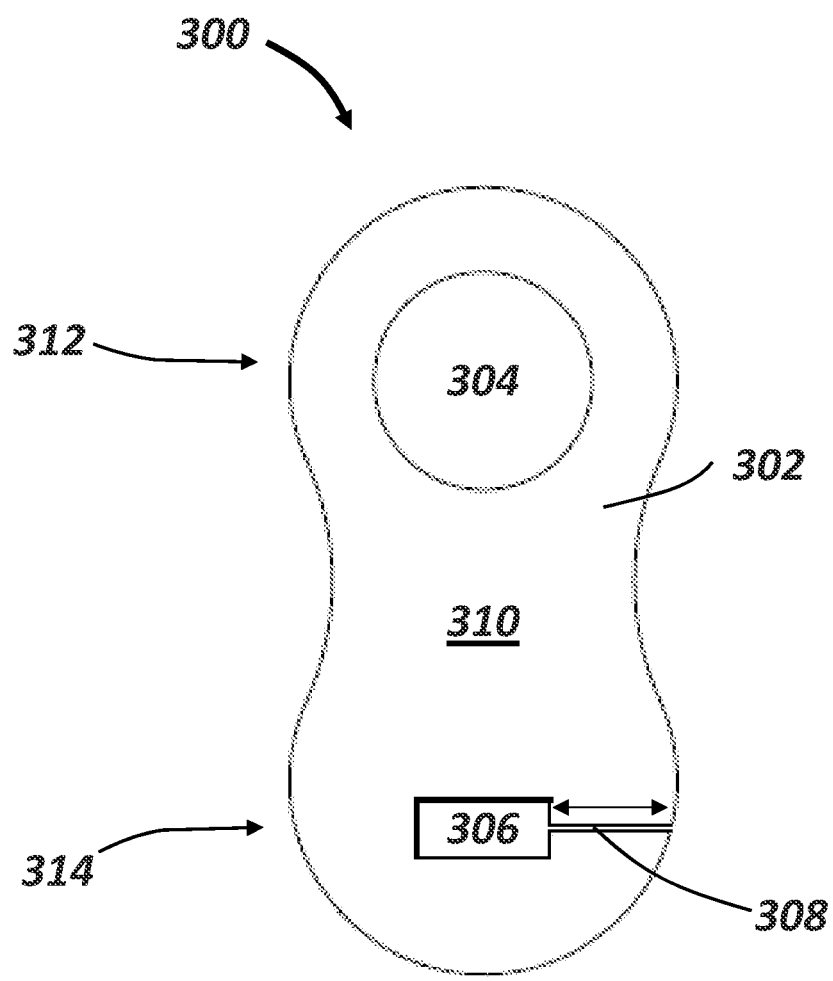
FIG. 3 illustrates an enlarged view of a proximal surface of another accessory device, as constructed in accordance with at least one embodiment.

FIG. 3 shows an accessory device 300 comprised of a body 302 defining a first aperture 304, a second aperture 306 and a third aperture in the form of a narrow slit 308, all visible at a proximal surface 310 of the device. The first aperture 304 can be defined within a first end 312 of the device, the second aperture 306 can be defined within a second end 314 of the device, opposite the first end, and the slit 308 can be defined within either or both the first end 312 and the second end 314 of the device.

The first aperture 304, or lumen, has a circular cross-section and a relatively large diameter relative to the apertures defined by the aforementioned accessory devices 100, 200. The larger diameter of the first aperture 304 equips the accessory device 300 to receive an elongate interventional device having a similarly large cross-sectional diameter, such as a balloon catheter, stent catheter, or sheath member.

The second aperture 306 has an approximately rectangular cross-section to accommodate a similarly shaped cross-section of another elongate interventional device, such as a push member or tab included at a proximal end of a guide extension catheter, an example of which is represented by the proximal tab 104 and push member 106 of FIG. 1A.

The slit 308 may function as a clamp mechanism used to accommodate differently sized interventional devices within the second aperture 306 and/or facilitate insertion and removal of the interventional device into/from the second aperture. For example, the slit 308 may flex to accommodate an imperfect fit between the second aperture 306 and an interventional device. Because the slit 308 is biased toward its resting state shown in FIG. 3, it may clamp tightly around an interventional device when flexed. The slit 308 may also enable lateral insertion and removal (indicated by double-sided arrow) of the interventional device accommodated by the second aperture 306 during a given operation. Such lateral insertion and removal may enable quick and easy attachment and detachment, respectively, of the accessory device 300 to and from an interventional device. Additional embodiments may include similar clamping mechanisms or "quick-release" mechanisms in the form of a breakaway feature, a hinged member, a spring-loaded member, a snap-fit member, or a mechanical clamp, for example, to enable easy detachment (or attachment) of the accessory device 300 from an elongate interventional device extended therethrough. Similar clamping mechanisms may alternatively or additionally be present in the first end 312 of the device and associated with first aperture 304.

Figure 4:
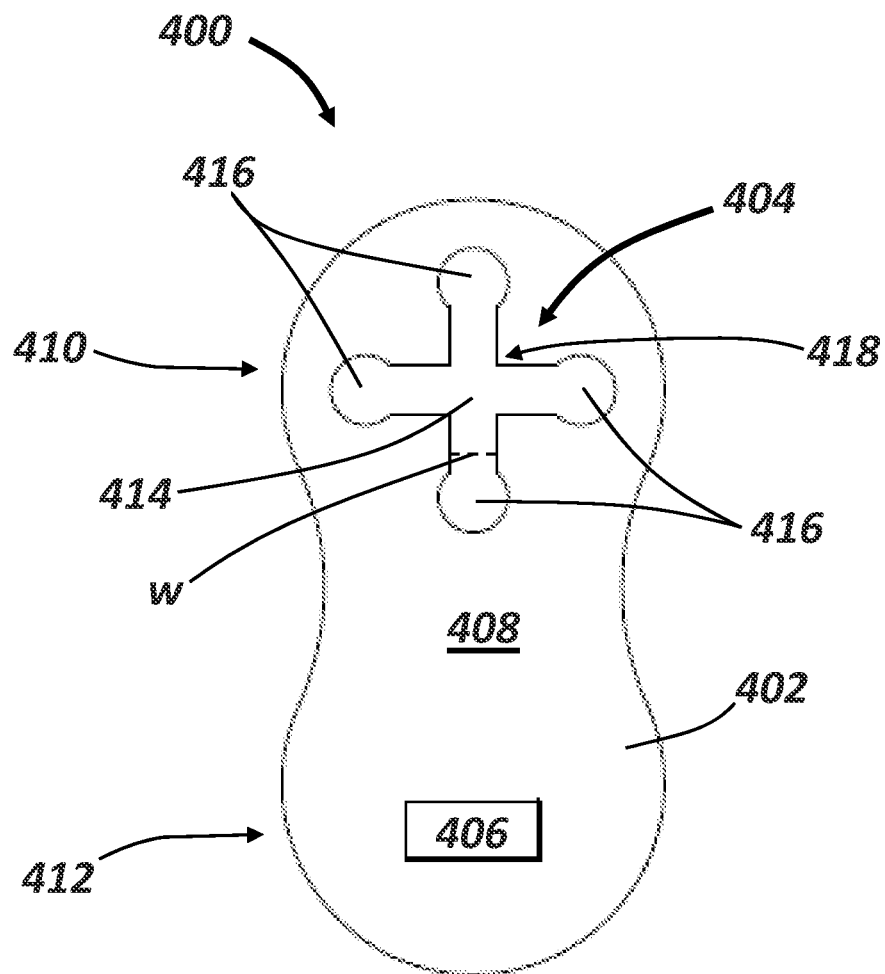
FIG. 4 illustrates an enlarged view of a proximal surface of another accessory device, as constructed in accordance with at least one embodiment.

FIG. 4 shows an accessory device 400 comprised of a body 402 defining a first lumen or aperture 404 and a second lumen or aperture 406, both visible at a proximal surface 408 of the device. The first aperture 404 is defined at a first end 410 of the accessory device 400, and the second aperture 406 is defined at a second end 412 of the accessory device 400. As further shown, the first aperture 404 comprises a cross-shaped lumen 414 defining a plurality of terminal nodes 416. Each of the nodes 416 can accommodate an elongate interventional device, which may be inserted first through a more central portion of the lumen 414 and then slid laterally toward a targeted node 416. The width w of each prong-like portion of the lumen 414 may be greater than the width of the slits shown in FIGS. 1-3 to accommodate interventional devices having greater cross-sectional widths and/or a greater number of interventional devices. In some examples, an interventional device having an irregular and/or large cross-section may be advanced through the center of the cross-shaped lumen 414. According to such examples, the corners 418 of the body 402 defined by the intersecting portions of the cross-shaped lumen 414 may flex to accommodate the shape and/or size of the interventional device.

The accessory devices disclosed herein may be provided as a kit with one or more additional devices, tools and/or other materials. For example, an accessory device may be provided with a hemostasis valve and at least one elongate medical device, e.g., guidewire or catheter, configured to be received and retained by the accessory device. The items included in a kit may be selected based on their common employment during a particular medical operation or class of operations. An accessory device can be included in a kit together with a guidewire and catheter pair, for instance, utilized for treating a particular type of vascular lesion, which may also be located at a specific anatomical location.

The accessory devices disclosed herein are configured for methods of catheter and/or guidewire management. For example, in one exemplary method, the device for catheter and/or guidewire management may be employed to treat various medical abnormalities, including vascular lesions, which may be treated in two or more vessels or branches simultaneously. Methods may target vascular abnormalities and/or non-vascular abnormalities. Another application is a method of deploying and using rapid exchange catheters. According to one or more of such applications, a clinician may advance a first elongate medical device through a first lumen or aperture of the accessory device, which is positioned outside the patient. Before or after a distal portion of the first elongate medical device reaches its anatomical target, e.g., lesion site, a second elongate medical device may be extended through a second lumen or aperture of the accessory device. One or more additional elongate medical devices may be advanced through one or more additional apertures defined by the device over the course of the medical operation. Embodiments may involve initially advancing an elongate medical device through a first aperture and then laterally sliding the elongate medical device through a narrow slit to a second aperture, such that the first aperture is configured to be utilized as a receiving aperture and the second aperture (and optionally the third, fourth, or fifth aperture, etc.) is configured to be utilized as a target aperture. One or more elongate medical devices can be removed from the accessory device by sliding the elongate medical device proximally or distally through its target aperture and/or sliding a proximal portion of the elongate medical device laterally through a slit connecting the aperture to a perimeter of the device. Methods may also involve sliding an elongate medical device distally and/or proximally through a lumen or aperture defined by the accessory device, and securing a proximal end portion of the elongate medical device in a narrow slit connected to the lumen or aperture. According to such example methods, the narrow slit may provide a clamping mechanism for temporarily securing the elongate medical device.

EXAMPLES

The above Detailed Description includes references to the accompanying drawings, which form a part of the Detailed Description. The Detailed Description should be read with reference to the drawings. The drawings show, by way of illustration, specific embodiments in which the present accessory devices and associated methods can be practiced. These embodiments are also referred to herein as "examples."

The Detailed Description is intended to be illustrative and not restrictive. For example, the above-described examples (or one or more features or components thereof) can be used in combination with each other. Other embodiments can be used, such as by one of ordinary skill in the art upon reviewing the above Detailed Description. Also, various features or components have been or can be grouped together to streamline the disclosure. This should not be interpreted as intending that an unclaimed disclosed feature is essential to any claim. Rather, inventive subject matter can lie in less than all features of a particular disclosed embodiment. Thus, the following claim examples are hereby incorporated into the Detailed Description, with each example standing on its own as a separate embodiment:

In Example 1, a device for managing elongate medical devices can include a body having proximal and distal surfaces and including at least first and second apertures extending through the body. The first aperture can be configured to be engageable with a proximal end portion of a first elongate medical device, and the second aperture can be configured to receive a second elongate medical device.

In Example 2, the device of Example 1 can optionally be configured such that the body is slidable along the proximal end portion of the first elongate medical device.

In Example 3, the device of any one of Examples 1 or 2 can optionally be configured such that the proximal surface of the body includes a funnel leading into the first aperture, the second aperture, or both.

In Example 4, the device of any one or any combination of Examples 1-3 can optionally be configured such that the body is incorporated into, or attached to, a proximal side of a hemostasis valve.

In Example 5, the device of any one or any combination of Examples 1~4 can optionally be configured such that the body is clampable to the proximal end portion of the first elongate medical device.

In Example 6, the device of any one or any combination of Examples 1-5 can optionally be configured such that the second aperture comprises a slit through the body, the slit configured to secure a guidewire or other small diameter elongate medical device.

In Example 7, the device of any one or any combination of Examples 1-6 can optionally be configured such that one or both of the first and second apertures includes a clamping mechanism configured to attach and detach the device from the first or second elongate medical device.

In Example 8, the device of Example 7 can optionally be configured such that the clamping mechanism comprises a slit extending from one or both of the first and second apertures to a perimeter of the body.

In Example 9, the device of any one or any combination of Examples 1-8 can optionally be configured such that the body has a thickness ranging from about 0.5 to about 3 centimeters, inclusive, as measured from the proximal surface to the distal surface.

In Example 10, the device of any one or any combination of Examples 1-9 can optionally be configured to further include a deformable membrane positioned within the first or second aperture.

In Example 11, the device of any one or any combination of Examples 1-10 can optionally be configured such that the body is manually deformable.

In Example 12, the device of any one or any combination of Examples 1-11 can optionally be configured such that the body has a Shore A durometer of between about 20 and about 60, inclusive.

In Example 13, the device of any one or any combination of Examples 1-12 can optionally be configured to further include a narrow slit extending between the first aperture and the second aperture.

In Example 14, the device of any one or any combination of Examples 1-13 can optionally be configured to include a third aperture positioned between the first aperture and the second aperture.

In Example 15, the device of Example 14 can optionally be configured to further include a first narrow slit extending between the first aperture and the third aperture and a second narrow slit extending between the second aperture and the third aperture.

In Example 16, the device of any one of Examples 14 or 15 can optionally be configured such that the third aperture has a larger diameter than the first and second apertures.

In Example 17, a method of securing elongate medical devices during a medical operation performed on a patient can involve advancing a first elongate medical device through a first aperture extending through a body of an accessory device, the accessory device having proximal and distal surfaces and positioned externally to the patient. The method can involve securing a proximal portion of the first elongate medical device within the first aperture, advancing a second elongate medical device through a second aperture extending through the body of the accessory device, and securing a proximal portion of the second elongate medical device within the second aperture.

In Example 18, the method of Example 17 can optionally be implemented such that securing the proximal portion of the first elongate device within the first aperture comprises allowing the body of the accessory device to grip the proximal portion of the first elongate medical device.

In Example 19, the method of any one of Examples 17 or 18 can optionally further involve removing the proximal portion of the first elongate medical device from the first aperture by laterally sliding the proximal portion through a slit connecting the first aperture to a perimeter of the accessory device.

In Example 20, the method of any one or any combination of Examples 17-19 can optionally be implemented such that the second aperture comprises a narrow slit configured to frictionally secure the proximal portion of the second elongate medical device.

In Example 21, the method of any one or any combination of Examples 17-20 can optionally be implemented such that the body of the accessory device further comprises a funnel leading into the first aperture, the second aperture, or both.

Closing Notes

Certain terms are used throughout this patent document to refer to particular features or components. As one skilled in the art appreciates, different people may refer to the same feature or component by different names. This patent document does not intend to distinguish between components or features that differ in name but not in function.

For the following defined terms, certain definitions shall be applied unless a different definition is given elsewhere in this patent document. The terms "a," "an," and "the" are used to include one or more than one, independent of any other instances or usages of "at least one" or "one or more." The term "or" is used to refer to a nonexclusive or, such that "A or B" includes "A but not B," "B but not A," and "A and B." All numeric values are assumed to be modified by the term "about," whether or not explicitly indicated. The term "about" generally refers to a range of numbers that one of skill in the art would consider equivalent to the recited value (e.g., having the same function or result). In many instances, the term "about" can include numbers that are rounded to the nearest significant figure. The recitation of numerical ranges by endpoints includes all numbers and sub-ranges within and bounding that range (e.g., 1 to 4 includes 1, 1.5, 1.75, 2, 2.3, 2.6, 2.9, etc. and 1 to 1.5, 1 to 2, 1 to 3, 2 to 3.5, 2 to 4, 3 to 4, etc.). The terms "patient" and "subject" are intended to include mammals, such as for human or veterinary applications. The terms "distal" and "proximal" are used to refer to a position or direction relative to the treating clinician. "Distal" and "distally" refer to a position that is distant from, or in a direction away from, the treating clinician. "Proximal" and "proximally" refer to a position that is near, or in a direction toward, the treating clinician.

The scope of the invention should be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended; that is, a device, kit or method that includes features or components in addition to those listed after such a term in a claim are still deemed to fall within the scope of that claim. Moreover, in the following claims, the terms "first," "second" and "third," etc. are used merely as labels, and are not intended to impose numerical requirements on their objects.

The Abstract is provided to allow the reader to quickly ascertain the nature of the technical disclosure. It is submitted with the understanding that it will not be used to interpret or limit the scope or meaning of the claims.

What is claimed is:

1. A device for managing elongate medical devices during a medical procedure, the device comprising:
   a body having a proximal surface, a distal surface opposite the proximal surface, and a lateral surface extending between the proximal surface and the distal surface, the lateral surface defining a thickness of the body ranging from about 0.5 cm to about 3 cm, inclusive;
   a first aperture and a second aperture, each extending through the body from the proximal surface to the distal surface at a location within a continuous perimeter of the body, the first aperture configured to be engageable with a proximal end portion of a first elongate medical device and the second aperture configured to receive a second elongate medical device; and
   a slit extending through the body from the proximal surface to the distal surface and having a first end terminating at the first aperture and a second end terminating at the second aperture such that the slit is positioned entirely within the continuous perimeter of the body,
   wherein the body is configured to be separate from, and proximally positioned to, a hemostasis valve used during the medical procedure.

2. The device of claim 1, wherein the body is slidable along the proximal end portion of the first elongate medical device.

3. The device of claim 1, wherein the proximal surface of the body includes a first funnel leading into the first aperture only and a second funnel leading into the second aperture only.

4. The device of claim 1, wherein the body is clampable to the proximal end portion of the first elongate medical device.

5. The device of claim 1, wherein the second aperture is configured to secure a guidewire or other small diameter elongate medical device.

6. The device of claim 1, further comprising a deformable membrane positioned within the first aperture or the second aperture.

7. The device of claim 1, wherein the body has a Shore A durometer of between about 20 and about 60, inclusive.

8. The device of claim 1, wherein the slit extending between the first aperture and the second aperture is configured to secure and retain a guidewire.

9. The device of claim 1, further comprising a third aperture positioned between the first aperture and the second aperture.

10. The device of claim 9, wherein the slit comprises a first slit portion extending between the first aperture and the third aperture and a second slit portion extending between the second aperture and the third aperture.

11. The device of claim 9, wherein the third aperture has a larger diameter than the first and second apertures.

12. The device of claim 1, further comprising:
   a fourth aperture and a fifth aperture, each extending through the body from the proximal surface to the distal surface and within the continuous perimeter of the body; and
   a second slit extending through the body and having a first end terminating at the fourth aperture and a second end terminating at the fifth aperture, wherein the second slit is positioned entirely within the continuous perimeter of the body.

13. The device of claim 12, wherein the first aperture, the second aperture, the third aperture, and the fourth aperture are equidistant from each other.

14. A method of securing elongate medical devices during a medical procedure performed on a patient, the method comprising:
   advancing a first elongate medical device through a first aperture extending through a body of an accessory device, the accessory device having a proximal surface, a distal surface opposite the proximal surface, and a lateral surface defining a thickness of the body ranging from about 0.5 cm to about 3 cm, the body positioned externally to the patient and separate from, and proximally positioned relative to, a hemostasis valve used during the medical procedure;
   securing a proximal portion of the first elongate medical device within a first aperture at a location within a continuous perimeter of the body;

advancing a second elongate medical device through a second aperture at a location within a continuous perimeter of the body extending through the body of the accessory device; and securing a proximal portion of the second elongate medical device within the second aperture, wherein the accessory device further comprises a slit extending through the body and having a first end terminating at the first aperture and a second end terminating at the second aperture, wherein the slit is positioned entirely within the continuous perimeter of the body.

15. The method of claim 14, wherein securing the proximal portion of the first elongate device within the first aperture comprises allowing the body of the accessory device to grip the proximal portion of the first elongate medical device.

16. The method of claim 14, further comprising removing the proximal portion of the first elongate medical device from the first aperture by laterally sliding the proximal portion through the slit.

17. The method of claim 14, wherein the slit is configured to frictionally secure the proximal portion of the second elongate medical device.

18. The method of claim 14, wherein the body of the accessory device further comprises a funnel leading into the first aperture only, the second aperture only, or both the first aperture and the second aperture.

19. The method of claim 14, wherein the proximal portion of the first elongate medical device and the proximal portion of the second elongate medical device are secured at a position proximal of the hemostasis valve used during the medical procedure.

20. The method of claim 14, wherein advancing the first elongate medical device through the first aperture includes advancing a proximal tab and an elongate push member through the first aperture.

* * * * *